(12) United States Patent
DiUbaldi

(10) Patent No.: US 8,352,026 B2
(45) Date of Patent: *Jan. 8, 2013

(54) IMPLANTABLE PULSE GENERATORS AND METHODS FOR SELECTIVE NERVE STIMULATION

(75) Inventor: Anthony DiUbaldi, Jackson, NJ (US)

(73) Assignee: Ethicon, Inc., Somerville, NJ (US)

( * ) Notice: Subject to any disclaimer, the term of this patent is extended or adjusted under 35 U.S.C. 154(b) by 1097 days.

This patent is subject to a terminal disclaimer.

(21) Appl. No.: 11/866,588

(22) Filed: Oct. 3, 2007

(65) Prior Publication Data

US 2009/0093858 A1    Apr. 9, 2009

(51) Int. Cl.
*A61N 1/00* (2006.01)

(52) U.S. Cl. ............................................. 607/2; 607/66

(58) Field of Classification Search .................. 607/2, 66
See application file for complete search history.

(56) References Cited

U.S. PATENT DOCUMENTS

| | | |
|---|---|---|
| 3,683,915 A | 8/1972 | Voss |
| 3,902,502 A | 9/1975 | Liss et al. |
| 3,933,147 A | 1/1976 | DuVall et al. |
| 3,941,136 A | 3/1976 | Bucalo |
| 4,406,288 A | 9/1983 | Horwinski |
| 4,537,195 A | 8/1985 | McDonnell |
| 4,719,922 A | 1/1988 | Padjen |
| 4,909,255 A | 3/1990 | Farin |
| 4,989,605 A | 2/1991 | Rossen |
| 5,167,237 A | 12/1992 | Rabin et al. |
| 5,350,414 A | 9/1994 | Kolen |
| 5,358,514 A | 10/1994 | Schulman |
| 5,421,817 A | 6/1995 | Liss et al. |
| 5,458,630 A | 10/1995 | Hoegnelid et al. |
| 5,464,434 A | 11/1995 | Alt |
| 5,476,481 A | 12/1995 | Schondorf |
| 5,487,759 A | 1/1996 | Bastyr et al. |
| 5,556,421 A | 9/1996 | Prutchi et al. |
| 5,558,640 A | 9/1996 | Pfeller et al. |
| 5,562,717 A | 10/1996 | Tippey |
| 5,617,876 A | 4/1997 | van Duyl |
| 5,645,062 A | 7/1997 | Anderson et al. |
| 5,702,428 A | 12/1997 | Tippey |

(Continued)

FOREIGN PATENT DOCUMENTS

CN    1593683    3/2005

(Continued)

OTHER PUBLICATIONS

International Search Report for International Application No. PCT/US2008/078361, mailed Jan. 27, 2009.

(Continued)

*Primary Examiner* — Eric D. Bertram
(74) *Attorney, Agent, or Firm* — Cheryl F. Cohen, LLC

(57) ABSTRACT

An Implantable Pulse Generator (IPG) includes a surgically implantable housing, a battery, a first waveform generator, a second waveform generator, a modulator, and electrodes. The IPG produces a pulse envelope, a carrier waveform, and a modulated waveform. The pulse envelope is a low frequency waveform with specific pulse width, amplitude and shape to selectively stimulate a target nerve or body part. The carrier waveform is a high frequency waveform with properties such as amplitude, frequency and the like chosen so as to overcome tissue impedance and the stimulation threshold of the target nerve. The modulated waveform is the waveform obtained by modulating the carrier waveform by the pulse envelope.

26 Claims, 10 Drawing Sheets

U.S. PATENT DOCUMENTS

| | | | |
|---|---|---|---|
| 5,722,996 A | 3/1998 | Bonnet et al. | |
| 5,730,125 A | 3/1998 | Prutchi et al. | |
| 5,735,887 A | 4/1998 | Barreras, Sr. et al. | |
| 5,791,344 A | 8/1998 | Schulman et al. | |
| 5,851,223 A | 12/1998 | Liss et al. | |
| 5,902,329 A | 5/1999 | Hoffmann et al. | |
| 5,984,854 A | 11/1999 | Ishikawa et al. | |
| 5,993,414 A | 11/1999 | Haller | |
| 6,035,236 A | 3/2000 | Jarding et al. | |
| 6,092,530 A | 7/2000 | Weissman et al. | |
| 6,099,479 A | 8/2000 | Christopherson et al. | |
| 6,155,267 A | 12/2000 | Nelson | |
| 6,164,284 A | 12/2000 | Schulman et al. | |
| 6,167,304 A | 12/2000 | Loos | |
| 6,183,461 B1 | 2/2001 | Matsuura et al. | |
| 6,199,575 B1 | 3/2001 | Widner | |
| 6,205,359 B1 | 3/2001 | Boveja | |
| 6,221,024 B1 | 4/2001 | Miesel | |
| 6,231,516 B1 | 5/2001 | Keilman et al. | |
| 6,240,317 B1 | 5/2001 | Villaseca et al. | |
| 6,263,246 B1 | 7/2001 | Goedeke et al. | |
| 6,285,897 B1 | 9/2001 | Kilcoyne et al. | |
| 6,298,272 B1 | 10/2001 | Peterfeso et al. | |
| 6,330,885 B1 | 12/2001 | Weissman et al. | |
| 6,354,991 B1 | 3/2002 | Gross et al. | |
| 6,360,129 B1 | 3/2002 | Ley et al. | |
| 6,366,814 B1 | 4/2002 | Boveja et al. | |
| 6,384,353 B1 | 5/2002 | Huang et al. | |
| 6,402,689 B1 | 6/2002 | Scarantino et al. | |
| 6,404,204 B1 | 6/2002 | Farruggia et al. | |
| 6,413,393 B1 | 7/2002 | Van Antwerp et al. | |
| 6,432,050 B1 | 8/2002 | Porat et al. | |
| 6,438,407 B1 | 8/2002 | Ousdigian et al. | |
| 6,442,413 B1 | 8/2002 | Silver | |
| 6,443,883 B1 | 9/2002 | Ostrow et al. | |
| 6,447,462 B1 | 9/2002 | Wallace et al. | |
| 6,459,933 B1 | 10/2002 | Lurie et al. | |
| 6,471,645 B1 | 10/2002 | Warkentin et al. | |
| 6,497,655 B1 | 12/2002 | Linberg et al. | |
| 6,505,074 B2 | 1/2003 | Boveja et al. | |
| 6,535,766 B1 | 3/2003 | Thompson et al. | |
| 6,560,490 B2 | 5/2003 | Grill et al. | |
| 6,567,706 B2 | 5/2003 | Bar-Or et al. | |
| 6,652,449 B1 | 11/2003 | Gross et al. | |
| 6,662,052 B1 | 12/2003 | Sarwal et al. | |
| 6,668,191 B1 | 12/2003 | Boveja | |
| 6,701,185 B2 | 3/2004 | Burnett et al. | |
| 6,712,772 B2 | 3/2004 | Cohen et al. | |
| 6,751,501 B1 | 6/2004 | Schuler et al. | |
| 6,836,684 B1 | 12/2004 | Rijkoff et al. | |
| 6,862,480 B2 | 3/2005 | Cohen et al. | |
| 6,879,859 B1 | 4/2005 | Boveja et al. | |
| 6,907,293 B2 | 6/2005 | Grill et al. | |
| 7,047,078 B2 | 5/2006 | Boggs, II et al. | |
| 7,062,330 B1 | 6/2006 | Boveja et al. | |
| 7,387,603 B2 | 6/2008 | Gross et al. | |
| 7,427,280 B2 | 9/2008 | Gerber | |
| 7,599,736 B2 | 10/2009 | DiLorenzo | |
| 7,676,271 B2 | 3/2010 | Wahlstrand et al. | |
| 7,815,895 B2 | 10/2010 | Katagiri et al. | |
| 8,170,683 B2 | 5/2012 | Wahlgren et al. | |
| 2001/0018606 A1 | 8/2001 | Ingle et al. | |
| 2001/0025137 A1 | 9/2001 | Webb et al. | |
| 2001/0051768 A1 | 12/2001 | Schulman et al. | |
| 2002/0001870 A1 | 1/2002 | Oda et al. | |
| 2002/0011592 A1 | 1/2002 | Matsuo | |
| 2002/0026141 A1 | 2/2002 | Houben et al. | |
| 2002/0026244 A1 | 2/2002 | Trieu | |
| 2002/0082480 A1 | 6/2002 | Riff et al. | |
| 2002/0103514 A1 | 8/2002 | Abrahamson | |
| 2002/0107540 A1 | 8/2002 | Whalen et al. | |
| 2002/0111542 A1 | 8/2002 | Warkentin et al. | |
| 2002/0133196 A1 | 9/2002 | Thompson | |
| 2002/0151816 A1 | 10/2002 | Rich et al. | |
| 2003/0004403 A1 | 1/2003 | Drinan et al. | |
| 2003/0004553 A1 | 1/2003 | Grill et al. | |
| 2003/0162021 A1 | 8/2003 | van Heerden et al. | |
| 2003/0204224 A1* | 10/2003 | Torgerson et al. ............... 607/48 |
| 2003/0212305 A1 | 11/2003 | Anderson et al. | |
| 2003/0220669 A1 | 11/2003 | Shealy | |
| 2003/0233137 A1 | 12/2003 | Paul | |
| 2004/0068203 A1 | 4/2004 | Gellman et al. | |
| 2004/0236194 A1 | 11/2004 | Meyer | |
| 2005/0177067 A1 | 8/2005 | Tracey et al. | |
| 2005/0277998 A1* | 12/2005 | Tracey et al. ................... 607/48 |
| 2006/0047325 A1 | 3/2006 | Thimineiur et al. | |
| 2006/0095090 A1 | 5/2006 | De Ridder | |
| 2006/0111756 A1 | 5/2006 | Chang | |
| 2006/0167500 A1 | 7/2006 | Towe et al. | |
| 2006/0195146 A1 | 8/2006 | Tracey et al. | |
| 2006/0195153 A1* | 8/2006 | DiUbaldi et al. ............... 607/41 |
| 2007/0162085 A1 | 7/2007 | DiLorenzo | |
| 2007/0167990 A1 | 7/2007 | Mangrum et al. | |
| 2007/0185541 A1 | 8/2007 | DiUbaldi et al. | |
| 2007/0219606 A1 | 9/2007 | Moreci et al. | |
| 2007/0233204 A1 | 10/2007 | Lima et al. | |
| 2007/0260288 A1 | 11/2007 | Gross | |
| 2008/0132962 A1 | 6/2008 | DiUbaldi et al. | |
| 2008/0132969 A1 | 6/2008 | Bennett et al. | |
| 2008/0147146 A1 | 6/2008 | Wahlgren et al. | |
| 2008/0161874 A1 | 7/2008 | Bennett et al. | |
| 2008/0293830 A1 | 11/2008 | Katagiri et al. | |
| 2009/0005713 A1 | 1/2009 | Podrazhansky et al. | |
| 2009/0048642 A1 | 2/2009 | Goroszeniuk | |
| 2009/0054952 A1 | 2/2009 | Glukhovsky et al. | |
| 2009/0093858 A1 | 4/2009 | DiUbaldi | |
| 2009/0132018 A1 | 5/2009 | DiUbaldi et al. | |
| 2009/0187230 A1 | 7/2009 | DiLorenzo | |
| 2010/0042018 A1 | 2/2010 | Kleinsinger | |
| 2010/0042180 A1 | 2/2010 | Mueller et al. | |
| 2010/0076533 A1 | 3/2010 | Dar et al. | |
| 2010/0249677 A1 | 9/2010 | DiUbaldi | |
| 2011/0264163 A1 | 10/2011 | Tracey et al. | |

FOREIGN PATENT DOCUMENTS

| | | |
|---|---|---|
| CN | 1745857 | 3/2006 |
| DE | 10033400 | 1/2001 |
| EP | 1048264 | 11/2000 |
| JP | 2000/316991 | 11/2000 |
| JP | 2001-259047 | 9/2001 |
| JP | 2003/135607 | 5/2003 |
| WO | 90/14127 | 11/1990 |
| WO | 97/18856 | 5/1997 |
| WO | 97/39796 | 10/1997 |
| WO | 99/55411 | 11/1999 |
| WO | 00/33738 | 5/2000 |
| WO | 00/33065 | 6/2000 |
| WO | 01/49369 | 7/2001 |
| WO | 01/56633 | 8/2001 |
| WO | 02/22008 | 3/2002 |
| WO | 02/27294 | 4/2002 |
| WO | 02/58551 | 8/2002 |
| WO | 02/62215 | 8/2002 |
| WO | 03/020364 | 3/2003 |
| WO | 03/030733 | 4/2003 |
| WO | 03/071944 | 9/2003 |
| WO | 2004/050172 | 6/2004 |
| WO | 2005/002663 | 1/2005 |

OTHER PUBLICATIONS

Written Opinion of the International Searching Authority for International Application No. PCT/US2008/078361, mailed Jan. 27, 2009.

Chinese Office Action and accompanying Chinese Search Report dated Jun. 27, 2012 (6 pages) for counterpart Chinese Patent Application No. 200880118949.4, filed on Oct. 1, 2008 claiming priority to the present application.

Becker, T.J., "Cardio MEMS Moves Closer to Commercializing its Innovative Heart Sensors", (Feb. 27, 2005) ATDC News & Information, Georgia Institute of Technology.

Chappel, J., Electronic News—Ambient Intelligence (Oct. 11, 2002).

Rousche, P.J. et al., "Flexibile Polyimide-Based Intracortical Electrode Arrays with Bioactive Capacity", IEEE Transactions on Biomedical Engineering, vol. 48, No. 3 (2001) pp. 361-371.

Siwapornsathain, E. et al., "Telemetry and Sensor Platform for Ambulatory Urodynamics", Proceedings of the 2nd Annual International IEEE-EMBS Special Topics Conference on Microtechnologies in Medicine & Biology, Madison, WI, May (2002).

Voskerician, G. et al., "Biocompatibility and biofouling of MEMS drug delivery devices", Biomaterials, 24 (2003) pp. 1959-1967.

Walter, et al., "Evaluation of a 316LVM Woven Eye Electrode for Direct Bladder Stimulation", Engineering in Medicine and Biology, vol. 13, No. 4 (1991) 00. 1853-1854.

Fiber Optic Sensors, Products Datasheet FOP—M Pressure Sensor (undated).

Frost & Sullivan Report 2002.

Rosell, J. et al., "Skin Impedance from 1 Hz to 1 MHz", IEEE Transactions on Biomedical Engineering, vol. 35, No. 8, Aug. 1988, pp. 649-651.

Reilly, J. Patrick, "Electrical Stimulation and Electropathology," Cambridge University Press (1992).

Junge et al., "Titanium Coating of a Polyproplyene Mesh for Hernia Repair: Efffect on Biocompatibility," Hernia vol. 6, No. 9, pp. 115-119, published on line Dec. 4, 2004.

* cited by examiner

IMPLANTABLE PULSE GENERATORS AND METHODS FOR SELECTIVE NERVE STIMULATION

BACKGROUND OF THE INVENTION

1. Field of the Invention

The present invention is generally related to stimulating nerves and body parts. More specifically, the present invention is related to implantable systems, devices, and methods for stimulating nerves and body parts to achieve therapeutic benefit.

2. Description of the Related Art

Nerves are part of the peripheral nervous system of a human body. They convey sensory signals from skin or organs to the central nervous system and vice versa. Nerves may suffer functional defects due to normal wear and tear, physical injuries, infection, and/or the failure of blood vessels surrounding the nerves. These functional defects may be accompanied by pain, numbness, weakness, and in some cases, paralysis. Other problems may include urinary or fecal incontinence. For example, with urinary incontinence, daily physical activities such as laughing, coughing, and sneezing may result in involuntary urination.

Different tactics have been developed to overcome the above-mentioned problems. One approach involves behavior modification such as urinating more frequently or wearing a protective pad or protective undergarments. In certain social situations, however, individuals may not be able to follow the practice of frequent urination or wearing protective garments. Another approach involves a medical therapy including taking prescribed drugs (e.g. pain medication). This methodology may result in adverse side effects or drug interactions, however, that will ultimately require discontinuation.

Yet another technique for overcoming the above-mentioned problems involves stimulating a nerve having a functional defect by using an electro-medical device that is positioned near a target nerve. One such electro-medical device is commonly referred to as an Implantable Pulse Generator (IPG). An IPG typically includes one or more electrodes, an electrical pulse generator, a battery, and a housing. The electrical pulse generator generates a waveform having a specific shape, form, and frequency range capable of stimulating a target nerve. When the electrodes receive the waveform from the generator, they draw energy from the battery and generate an electric field of suitable strength to stimulate the target nerve.

IPG's have proven to be somewhat effective for stimulating nerves. One of the problems associated with IPG's, however, is that they consume a significant amount of power. Causes of high power consumption include an increase in electrical impedance between the electrodes, or an increase in electrical impedance between the electrodes and the IPG. This may happen due to several factors such as electrode migration, encapsulation of one or more electrodes, and material property changes in the electrodes or body tissue. Material property changes in the electrodes may occur due to a number of factors including chemical changes caused by body fluids being present at the surface of the electrodes, frequent passing of electrical current through the tissue, and normal wear and tear occurring during daily activities.

Higher battery power consumption may also be caused by a phenomenon referred to as "desensitization of stimulus," whereby the human body responds to an applied external charge by offering a resistance to the applied external charge. The body resists the applied external charge by increasing the stimulation threshold for a target nerve, thereby rendering the earlier stimulus level ineffective. To overcome this problem, a more powerful charge must be generated, which consumes even more battery power. This requires frequent replacement and/or recharging of the batteries.

In other prior art IPG's, it has been observed that the generated electric field spreads widely, affecting untargeted muscles and nerves along with the target nerve. The wide spreading of the electric field significantly reduces the strength of the electrical signal at the target nerve. In order to properly stimulate the target nerve, the strength of the electrical signal must be substantially increased. This requires the waveform generators to draw more power from the battery. Moreover, these prior art IPG's unnecessarily stimulate untargeted nerves and body parts.

Thus, there remains a need for improved devices and methods of stimulating body parts and nerves. There also remains a need for improved implantable systems and devices that more effectively stimulate target nerves and body parts, while not stimulating untargeted nerves and body parts. Furthermore, there remains a need for implantable systems, devices and methods that are less invasive, and that require less power to operate effectively, thereby minimizing the need to replace and/or recharge power sources.

SUMMARY OF THE INVENTION

The present invention relates to systems, devices and methods for stimulating nerves and body parts. In one embodiment, the system includes an implantable electro-medical device for selectively stimulating targets nerves and body parts. The implantable electro-medical device desirably generates and applies modulated waveforms that effectively pass through the body for stimulating nerves and body parts. The efficiency results in a device that consumes less battery power and operates for a longer period of time before being recharged.

The implantable electro-medical device, also referred to as an Implantable Pulse Generator (IPG), is preferably surgically implanted in the body. In one embodiment, the IPG is placed near a target nerve to be stimulated. The IPG desirably generates a modulated waveform that enables the IPG to be placed further from the target nerve without requiring an increase in output intensity. The IPG may also generate a modulated waveform that stimulates a target nerve while using less power than is required when using a conventional IPG.

In one embodiment of the present invention, the IPG may include one or more electrodes, one or more waveform generators, one or more modulators, a battery, and a housing. The waveform generators preferably generate waveforms capable of selectively stimulating target nerves and penetrating the tissues between the IPG and the target nerves. A battery is a preferred power source for the IPG, and the waveform generators draw power from the battery. The modulator modulates the waveforms from the waveform generator to produce a modulated waveform, and sends it to the electrodes. Upon receiving the electrical signals from the modulator, the electrodes desirably generate an electric field for stimulating the target nerve.

In one embodiment of the present invention, the battery is a non-rechargeable battery. In another embodiment of the present invention, the battery is a rechargeable battery, which may be recharged using a radio frequency signal, by using inductive coupling to transfer energy through a shared magnetic field, or by using any other known technique for recharging power sources. The housing of the IPG is preferably biocompatible so that it may be conveniently implanted in a human body.

Although the present invention is not limited by any particular theory of operation, it is believed that each nerve has unique physical properties that are attributable to neurons, which are the building blocks of the nerve. The physical properties of a neuron, such as diameter, length, and myelination, determine capacitance and conduction velocity of electrical signals in the nerve. Thus, each nerve can be selectively stimulated by applying a waveform having a particular frequency.

Typically, the excitation frequency of the target nerve lies in the range of 10-40 Hz. The electrical signals with such a low frequency cannot overcome the tissue impedance offered by the tissues between the electrodes and the target nerve that may be caused by encapsulation of the electrodes, or electrode migration over time. The IPG of the present invention transmits a controlled, amplitude-modulated waveform composed of a carrier signal and a pulse envelope. The carrier waveform is designed to be of sufficient frequency to overcome tissue impedances. The pulse envelope contains specific pulse width, amplitude and shape information designed to stimulate specific nerves. The high frequency carrier signal can be used to pass through high impedance tissue (subcutaneous or transcutaneous) while the modulating signal is used to activate nervous tissue.

The present invention can be applied to other areas of the body where tissue impedance characteristics decrease at higher frequencies. Namely, this waveform can be applied to subcutaneous tissue and encapsulations that typically surround implanted IPG's and electrodes. The benefits of this technology can be in the form of reduced power consumption as the efficiency of the delivered signal is increased, and in a reduction in collateral, unwanted, nerve activation by way of low power stimulation.

In one or more embodiments of the present invention, the implantable electro-medical device is adapted to generate a modulated waveform for stimulating a target nerve using the devices and techniques described in commonly assigned United States Patent Application Publication Nos. US 2005/0277998 (U.S. application Ser. No. 11/146,522, filed Jun. 7, 2005), and US 2006/0195153 (U.S. Appln. No. 11/343,627, filed Jan. 31, 2006), the disclosures of which are hereby incorporated by reference herein. The waveform is desirably generated by modulating a carrier waveform with a pulse envelope. Properties of the carrier waveform such as amplitude, frequency, and the like, are chosen so as to overcome the tissue impedance and the stimulation threshold of the target nerve. The pulse envelope is a waveform having a specific pulse width, amplitude and shape designed to selectively stimulate the target nerve. This waveform is able to penetrate efficiently through the tissue to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves are not stimulated.

In one embodiment, an implantable pulse generator for stimulating nerves or body parts includes a first waveform generator adapted to generate a first waveform having a first frequency, a second waveform generator adapted to generate a carrier waveform having a second frequency that is higher than the first frequency, a modulator electrically coupled to the first and second waveform generators and adapted to modulate the first waveform and the carrier waveform to generate a modulated waveform, and an electrode electrically coupled to the modulator for applying the modulated waveform. The implantable pulse generator may include a power source, such as a battery, for providing power to the waveform generators and the modulator. In one embodiment, the first and second waveform generators, the modulator, and the battery are disposed within a surgically implantable housing. In one preferred embodiment, the said first waveform has a frequency adapted to stimulate a target nerve or a target body part. The first waveform may have a frequency substantially within the range of 10-40 Hz, and the carrier waveform may have a frequency substantially within the range of 10-400 KHz.

In one preferred embodiment, the implantable pulse generator may include a microprocessor adapted to receive biofeedback data, and control operation of the first and second waveform generators in response to the biofeedback data. The implantable pulse generator also desirably includes a receiving device adapted to receive the biofeedback data, the receiving device being in communication with the microprocessor for providing the biofeedback data thereto. The implantable pulse generator may also include at least one sensor in communication with the receiving device, whereby the at least one sensor is adapted to sense one or more physiological conditions of a mammal, such as bladder pressure. A transmitter may be coupled with the at least one sensor for transmitting the one or more sensed physiological conditions. The transmitter may be a wireless transmitter.

In one embodiment of the present invention, an implantable pulse generator may include a third waveform generator adapted to generate a third waveform having a third frequency that is different from and out of phase with the first waveform, whereby the modulator is electrically coupled with the third waveform generator and is adapted to modulate the carrier waveform, the first waveform and the third waveform to generate the modulated waveform. The first waveform may be adapted to stimulate a first target nerve or body part and the third waveform may be adapted to stimulate a second target nerve or body part. In one embodiment of the present invention, the first waveform has a frequency of approximately 20 Hz, the third waveform has a frequency of approximately 10 Hz, and the carrier waveform has a frequency of approximately 10-400 KHz.

In one embodiment of the present invention, an implantable pulse generator may include a fourth waveform generator adapted to generate a fourth carrier waveform having a frequency different than the second carrier waveform, whereby the modulator further modulates the fourth carrier waveform to generate a modulated signal package. The modulator may include a first modulator for modulating the first waveform and the second carrier waveform to generate a first modulated signal, a second modulator for modulating the third waveform and the fourth carrier waveform to generate a second modulated signal, and a third modulator for modulating the first and second modulated signals to generate a modulated signal package.

In another embodiment of the present invention, an implantable system for stimulating nerves or body parts includes a first waveform generator adapted to generate a first waveform having a frequency capable of stimulating a body part or a nerve, a second waveform generator adapted to generate a carrier waveform having a second frequency capable of passing through tissue of a mammal, a modulator electrically coupled to the first and second waveform generators and adapted to modulate the first waveform and the carrier waveform to generate a modulated waveform, a power source for operating the system, a surgically implantable housing containing the first and second waveform generators, the modulator, and the power source, and one or more electrodes electrically coupled to the modulator for applying the modulated waveform. The one or more electrodes may be surgically implantable.

The implantable system may include a microprocessor adapted to receive biofeedback data and control operation of the first and second waveform generators in response to the biofeedback data, and at least one sensor in communication with the microprocessor that is adapted to sense one or more physiological conditions of a mammal. The system may also include a third waveform generator adapted to generate a third waveform having a third frequency that is different from and out of phase with the first waveform, whereby the modulator is electrically coupled with the third waveform generator and is adapted to modulate the carrier waveform, the first waveform, and the third waveform to generate the modulated waveform. The first waveform is desirably adapted to stimulate a first body part and the third waveform is desirably adapted to stimulate a second body part.

in another preferred embodiment of the present invention, a method for stimulating body parts includes providing an implantable pulse generator having a first waveform generator adapted to generate a first waveform having a first frequency capable of stimulating a body part, a second waveform generator adapted to generate a carrier waveform having a frequency capable of passing through tissue of a mammal, a modulator electrically coupled to the first and second waveform generators and adapted to modulate the first waveform and the carrier waveform to generate a modulated waveform, a power source for providing power to the first and second waveform generators and the modulator, a housing containing the first and second waveform generators, the modulator and the power source, and an electrode electrically coupled to the modulator for applying the modulated waveform. The method desirably include surgically implanting the housing in a mammal, generating the first waveform and the carrier waveform, modulating the first waveform with the carrier waveform to produce a modulated signal, and applying the modulated signal to the target body part or nerve. The method may include implanting a sensor in the mammal, obtaining biofeedback data using the sensor, and using the biofeedback data for controlling generation of the first and second waveforms by the first and second waveform generators.

In one embodiment, the implantable pulse generator may include a third waveform generator adapted to generate a third waveform having a frequency capable of stimulating a second target nerve or body part. The method may include generating the third waveform out of phase with the first waveform, modulating the first waveform, the carrier waveform, and the third waveform to create a modulated signal package, and applying the modulated signal package to one or more body parts or nerves of the mammal. The method may also include generating a fourth carrier waveform having a frequency different than the second carrier waveform, whereby the modulating step includes modulating the first waveform and the second carrier waveform to create a first modulated signal, and modulating the third waveform and the fourth carrier waveform to create a second modulated signal.

Although one or more embodiments of the present invention are described in relation to nerve stimulation in females and the female urinary system, it is to be understood that the present invention may be readily adapted for nerve stimulation in males, children, and adults, and use in the urinary system or males, children, and adults. Further, the inventive principles, apparatus and methods disclosed herein may also have application to assessing and treating functionality in other areas, such as coronary or pulmonary functionality. Still further, the inventive principles, apparatus and methods disclosed herein may have application for stimulating various other nerves, such as stimulation of nerves during labor and delivery, or selectively stimulating branches of a given nerve bundle to selectively address different patient conditions. In addition, the technology described herein can be applied to various components of the nervous system that contribute or effect the following conditions: stress urinary incontinence, anal and fecal incontinence, sexual dysfunction, interstitial cystitis, chronic pain such as but not limited to pelvic pain, nocturia, and gastrointestinal disorders such as but not limited to gastric pacing. Moreover, the present invention may be used to stimulate body parts other than nerves, such as glands that secrete hormones, and large muscle groups, such as biceps muscle stimulation associate with physical therapy.

These and other preferred embodiments of the present invention will be described in more detail below.

BRIEF DESCRIPTION OF THE DRAWING

So the manner in which the above recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments encompassed within the scope of the present invention. Thus, the drawings are not to be considered limiting, for the present invention may admit to other equally effective embodiments, wherein.

DETAILED DESCRIPTION

Figure 1:
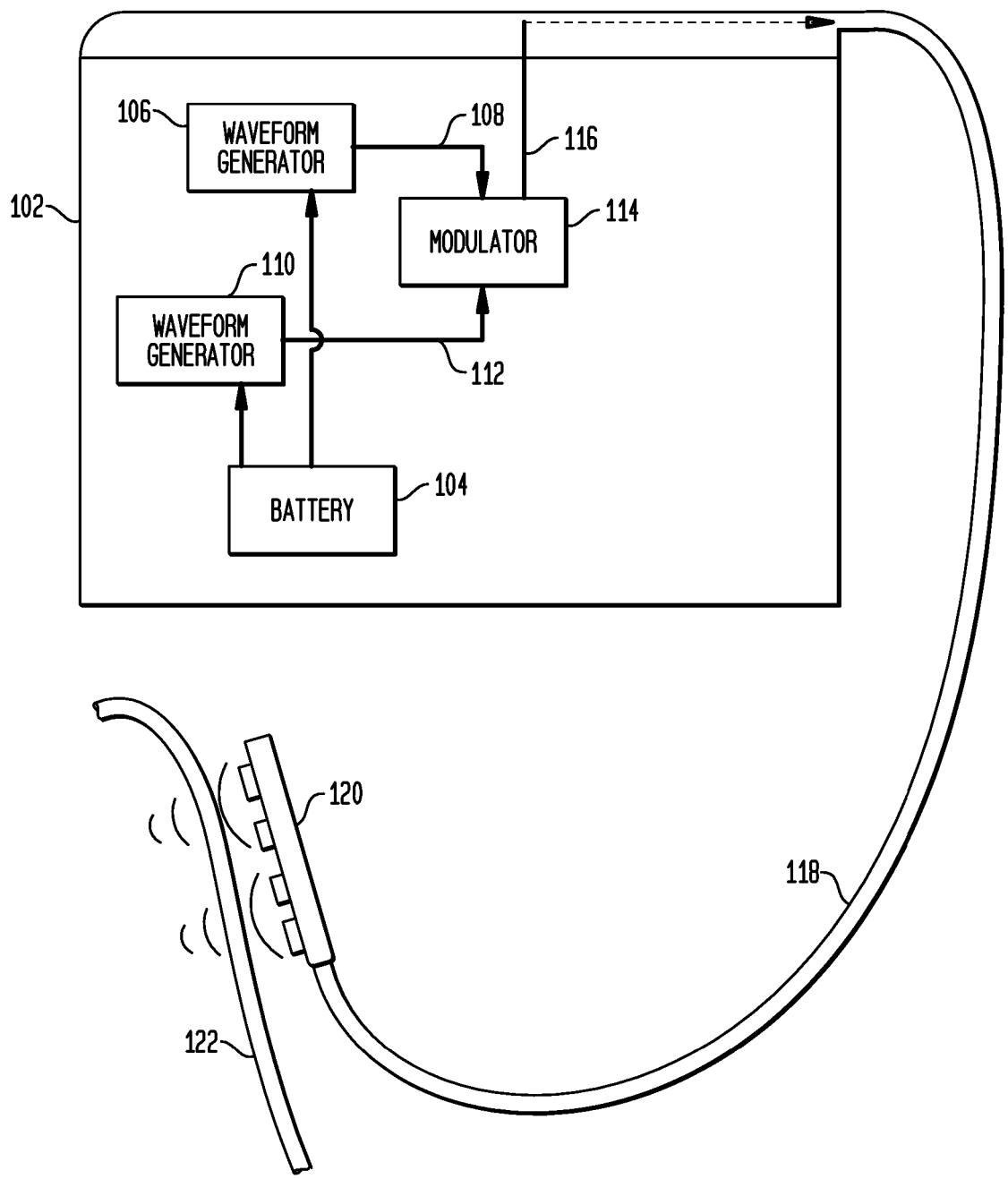
FIG. 1 shows an implantable pulse generator for stimulating body parts, in accordance with one preferred embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

The invention disclosed herein is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although one embodiment of the present invention is described in relation to nerve stimulation in females, it is to be understood that it can be readily adapted for use in males, and children. The inventive principles, apparatus and methods disclosed herein may also have application for stimulating various other nerves, either independently or simultaneously, such as stimulation of nerves during labor and delivery, or selectively stimulating branches of a given nerve bundle to selectively address different patient conditions. Thus, the present invention can, for example, be used to selectively treat or affect one or more of the following conditions simultaneously: stress urinary incontinence, anal and fecal incontinence, pain, sexual dysfunction, interstitial cystitis, chronic pain such as but not limited to pelvic pain, nocturia, and gastrointestinal disorders such as but not limited to gastric pacing. Finally, the present invention as described herein can also be used to stimulate body parts other than nerves, such as glands that secrete hormones, and large muscle groups, such as biceps muscle stimulation associated with physical therapy.

As indicated above, it is known that implantable pulse generators (IPG) can be used to stimulate both nerves and muscles within the body. One problem with conventional IPG devices is that the applied electrical signals tend to spread widely, affecting untargeted muscles and nerves as well as targeted ones. Further, to account for this signal dissipation, the applied current levels must be significantly increased to ensure adequate current densities at the targeted site. Another challenge associated with the application of electrical signals is that many nerves are stimulated by a low frequency signal, on the order of 10-40 Hz. Such a low frequency signal, however, cannot pass through body tissue to reach the target nerve(s). Many of these challenges have been overcome by the present invention, which will now be described in detail below.

Referring to FIG. 1, in one embodiment of the present invention, an implantable pulse generator 100 includes a housing 102 that is implantable in a human body. The housing 102 is preferably made of a biocompatible material. The implantable pulse generator 100 includes a suitable power source 104, such as a lithium battery, a first waveform generator 106, and a second waveform generator 110. The first and second waveform generators 106, 110 are electrically coupled to and powered by the battery 104. The waveform generators 106, 110 may be of any suitable type, such as those sold by Texas Instruments of Dallas, Tex. under model number NE555. The first waveform generator 106 generates a first waveform 108 having a frequency known to stimulate nerves in the body. In one embodiment, the frequency is within the range of about 10-30 Hz. In another embodiment, the frequency is within the range of about 10-40 Hz. As noted above, such low frequency signals (e.g. 10-40 Hz.) cannot, in and of themselves, pass through body tissue to effectively stimulate target nerves. In order to overcome this problem, the implantable pulse generator 100 has a second waveform generator 110 that generates a second waveform 112 having a higher frequency. The second waveform has a frequency of approximately 10-400 KHz. The second waveform 112 is applied along with the first waveform 108 to an amplitude modulator 114, such as the modulator having the designation On-Semi MC1496, which is sold by Texas Instruments.

Figure 2:
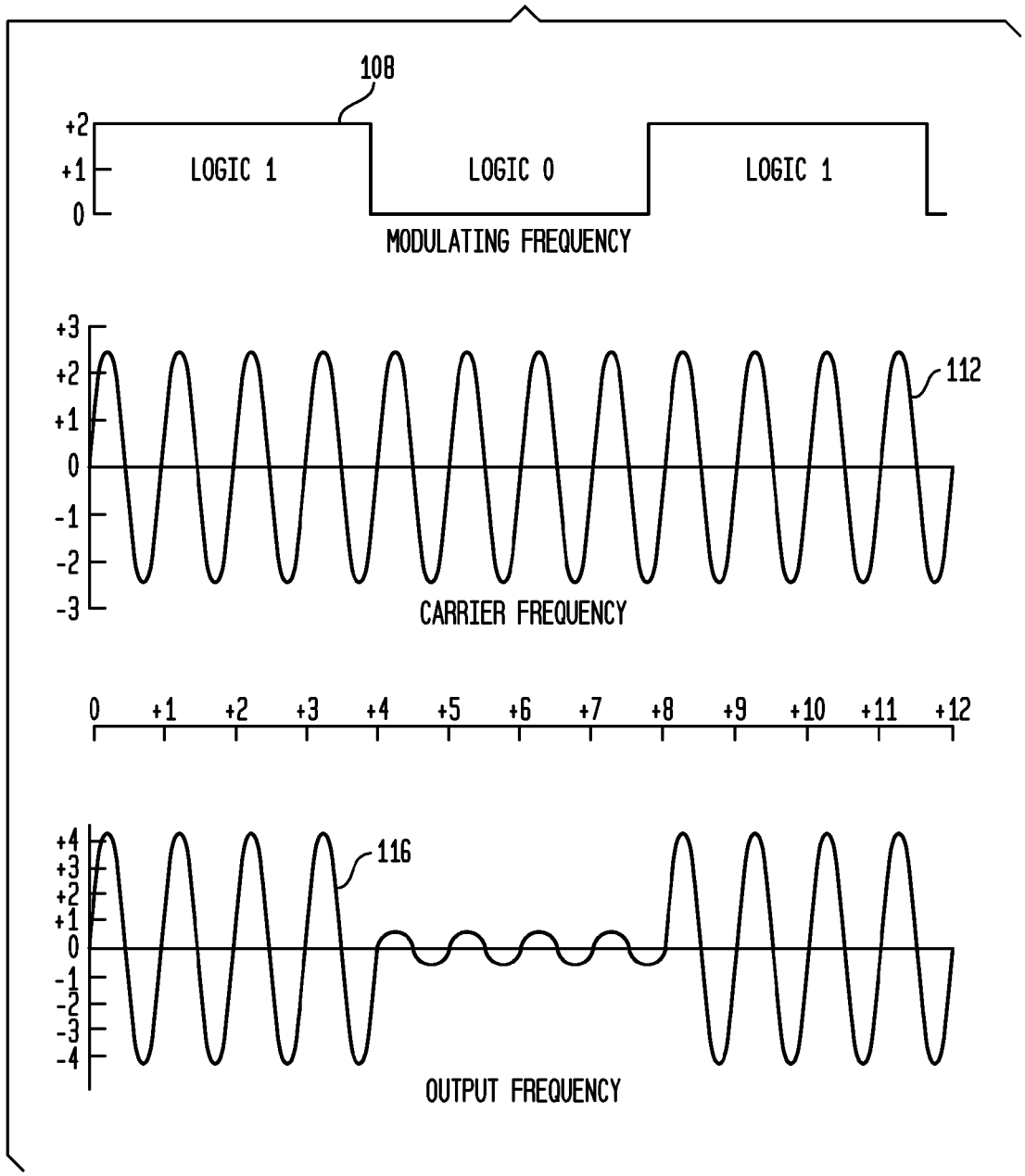
FIG. 2 shows exemplary waveforms generated by the implantable pulse generator shown in FIG. 1.

The modulator 114 generates a modulated waveform 116 that is transmitted through a lead 118 to electrodes 120. In certain preferred embodiments, the lead 118 is flexible. The electrodes 120, in turn, apply the modulated waveform 116 to the target nerve 122 to stimulate the target nerve. Referring to FIGS. 1 and 2, the first waveform 108 is preferably a square wave having a frequency of approximately 10-40 Hz, and the second waveform 112 is preferably a sinusoidal signal having a frequency in the range of 10400 KHz. The above-listed frequency ranges are merely exemplary so that other frequency ranges may be utilized and still fall within the scope of the present invention. As those skilled in the art will readily recognize, modulation of the first waveform 108 with the second waveform (carrier wave) 112 results in a modulated waveform or signal 116 having the configuration shown in FIG. 2.

Figure 3:
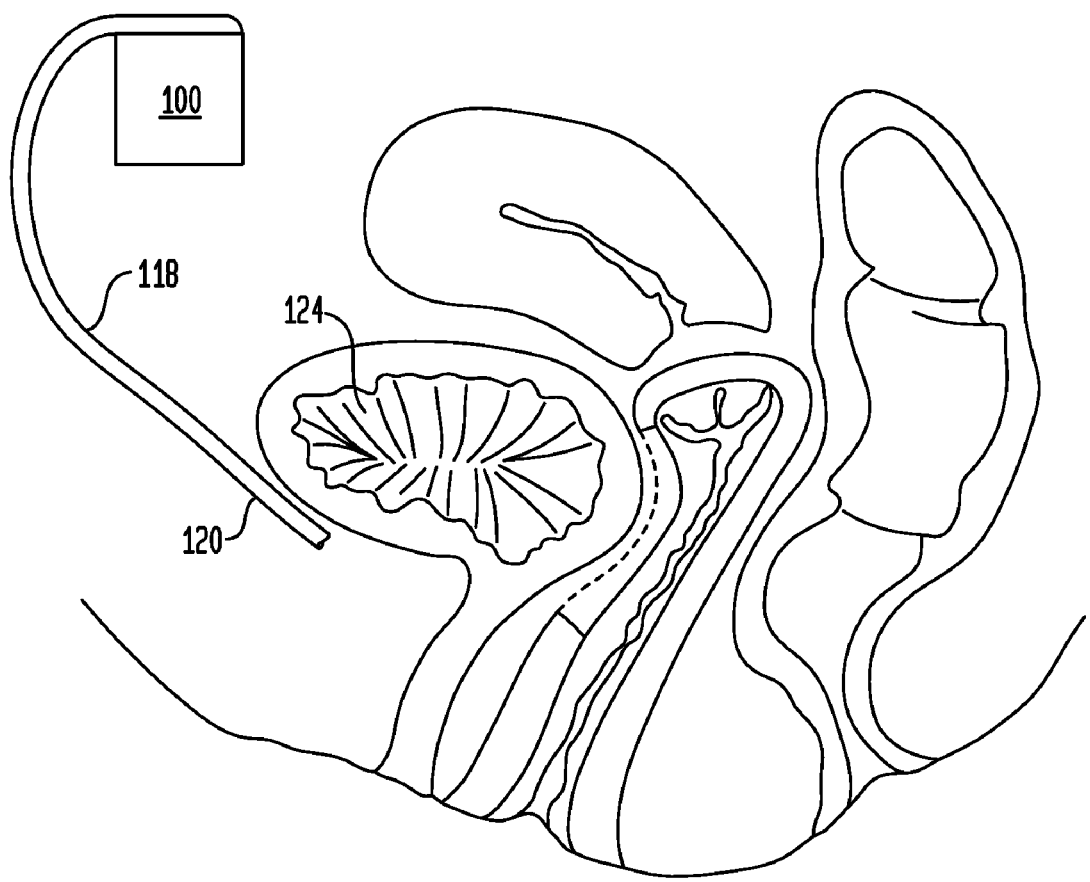
FIG. 3 shows the implantable pulse generator of FIG. 1 after being surgically implanted in a body.

Referring to FIG. 3, in one embodiment of the present invention, the implantable pulse generator (IPG) 100 is implanted in a body for treating a bladder problem. The IPG 100 includes a flexible lead 118 having one or more electrodes 120 provided at a distal end thereof. The electrodes 120 are adapted to apply modulated waveform signals to one or more target nerves (not shown) associated with the bladder 124. The modulated waveform includes the high frequency carrier waveform that is capable of easily propagating through the body tissue and the low frequency signal that is adapted to stimulate the target nerve(s) for the bladder 124.

Referring to FIG. 2, although the present invention is not limited by any particular theory of operation, it is believed that generating a modulated signal 116 enables transmission of the nerve stimulating waveform 108 through tissue due to the high frequency nature of the carrier waveform 112 that effectively carries the low frequency waveform 108 to the target nerve.

An underlying principal of operation of the present invention is the fact that nerves within the body can be selectively targeted for stimulation without affecting adjacent neurons. As is well known to those skilled in the art, bioelectric potentials are produced as a result of electrochemical activity of excitable cells found within nervous system tissue. These excitable cells exist in two electrical states, resting potential or action potential. Cells remain in the resting potential state until adequate stimulus is provided to cause the cells to reach the action or threshold potential, at which time the nerve "fires," and the action potential travels at a constant conduction velocity unattenuated along the cell membranes. This all-or-nothing response of the action potential causes the cell's membrane potential to go through a characteristic repeatable cycle, where the potential first goes from the negative resting potential, to a positive action potential, and then back down to the negative resting potential again all within approximately 1 ms. The response remains the same regardless of the magnitude of the stimulus, so long as the stimulus exceeds the threshold potential.

When an excitable cell membrane has an action potential response (from an adequate stimulus), its ability to respond to a second stimulus is significantly altered. During the initial depolarizing portion of the action potential, the cell membrane cannot respond to additional stimulus regardless of its intensity. This period is referred to as the absolute refractory period. Immediately following the absolute refractory period is a period referred to as a relative refractory period. During the relative refractory period, the cell membrane can respond only to intense stimulation. The existence of the absolute and relative refractory periods results in an upper frequency limit at which a cell can be repeatedly discharged. Thus, neurons can be seen as frequency dependent devices. The frequency dependent component of the neuron depends on its total capacitance, which will vary from neuron to neuron and will be a function of its length, diameter, coating (myelination) and the permeativity of the dielectric medium. In other words, for any given dielectric medium, varying either the length or diameter of the neuron, or its myelination, will vary its total capacitance.

Since neurons in the human body do vary greatly in diameter, length and myelination, the capacitance and conduction velocity (operating frequency) for these neurons vary as well. Using the differences in physical characteristics of adjacent neurons, selected nerves can be targeted for stimulation without affecting adjacent neurons. That is, selective neural stimulation can be achieved by characterizing the frequency response (capacitance) of adjacent neurons, and tuning the stimulation frequency to an area of noverlap. For example, for two adjacent neurons, where neuron A has a frequency band of operation from 0-20 Hz and neuron B has a frequency band of operation from 20-30 Hz, neuron B can be selectively stimulated with no effect on neuron A. Further, neuron A can be selectively stimulated even in an overlapping frequency range if stimulation is applied during neuron B's absolute refractory period, during which no amount of stimulation will cause neuron B to fire as discussed above, or if the stimulation is less than the magnitude required to cause stimulation during the relative refractory period. As described further herein, these principles can be applied to achieve selective stimulation of two or more nerves within the body.

Figure 4:
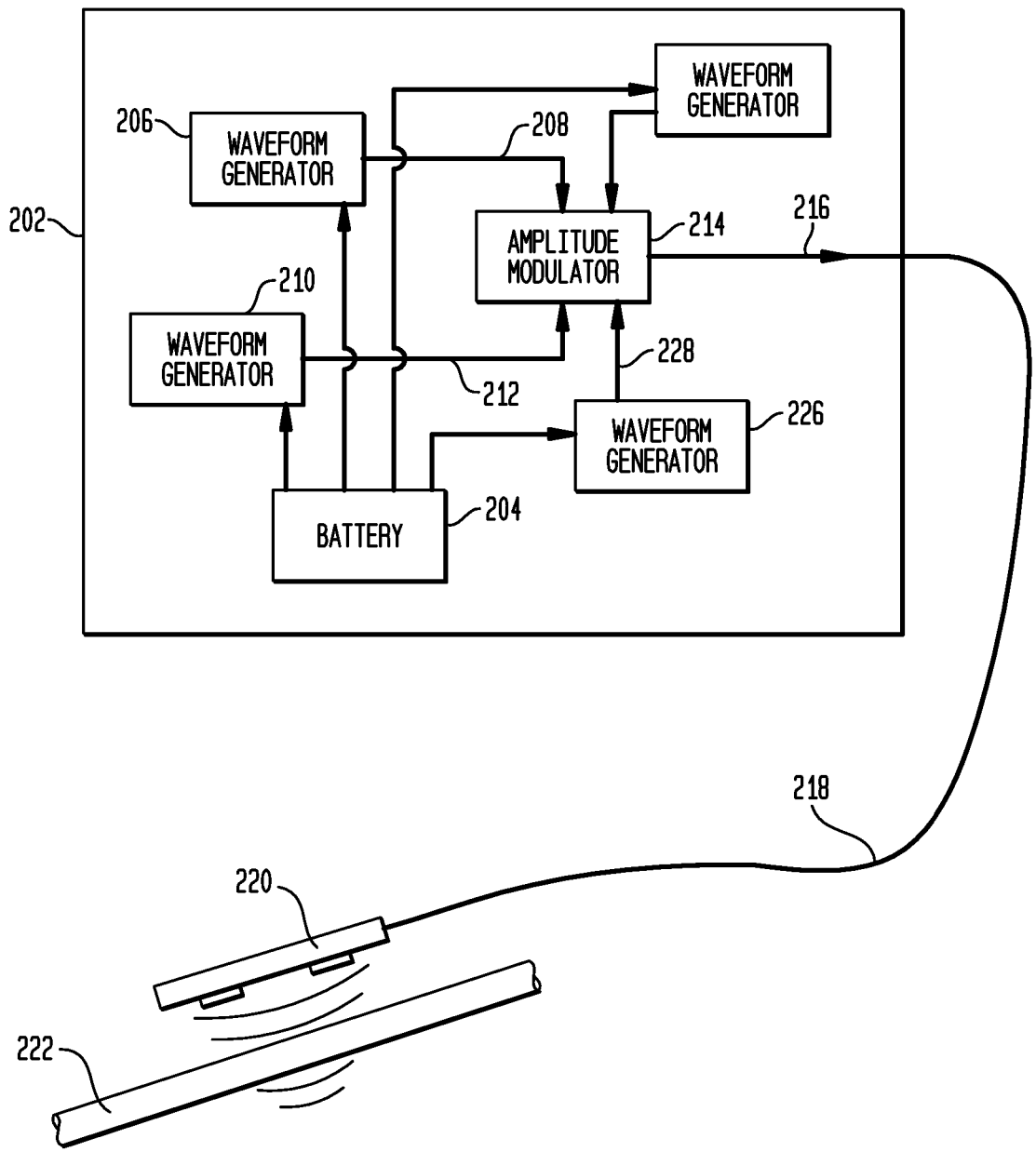
FIG. 4 shows an implantable pulse generator for stimulating body parts, in accordance with another preferred embodiment of the present invention.

Referring to FIG. 4, in one embodiment of the present invention, an implantable pulse generator 200 includes a housing 202 that is implantable in a body of a mammal (e.g. a human). The implantable pulse generator (IPG) 200 includes a suitable power source 204, such as a lithium ion battery, a first waveform generator 206 that produces a first waveform 208, a second waveform generator 210 that produces a second waveform 212, and a third waveform generator 226 that produces a third waveform 228. The first, second, and third waveform generators 206, 210, and 226 are preferably electrically coupled to and powered by the battery 204. These waveform generators may be of any suitable type, such as those sold by Texas Instruments of Dallas, Tex. under model number NE555. The output of the first 206, second 210 and third 226 waveform generators are applied to amplitude modulator 214, which modulates the three waveforms into a modulated signal package 216. The term "signal package" is used herein to describe a single output signal consisting or two or more individual signals modulated together in any way.

Figure 5:
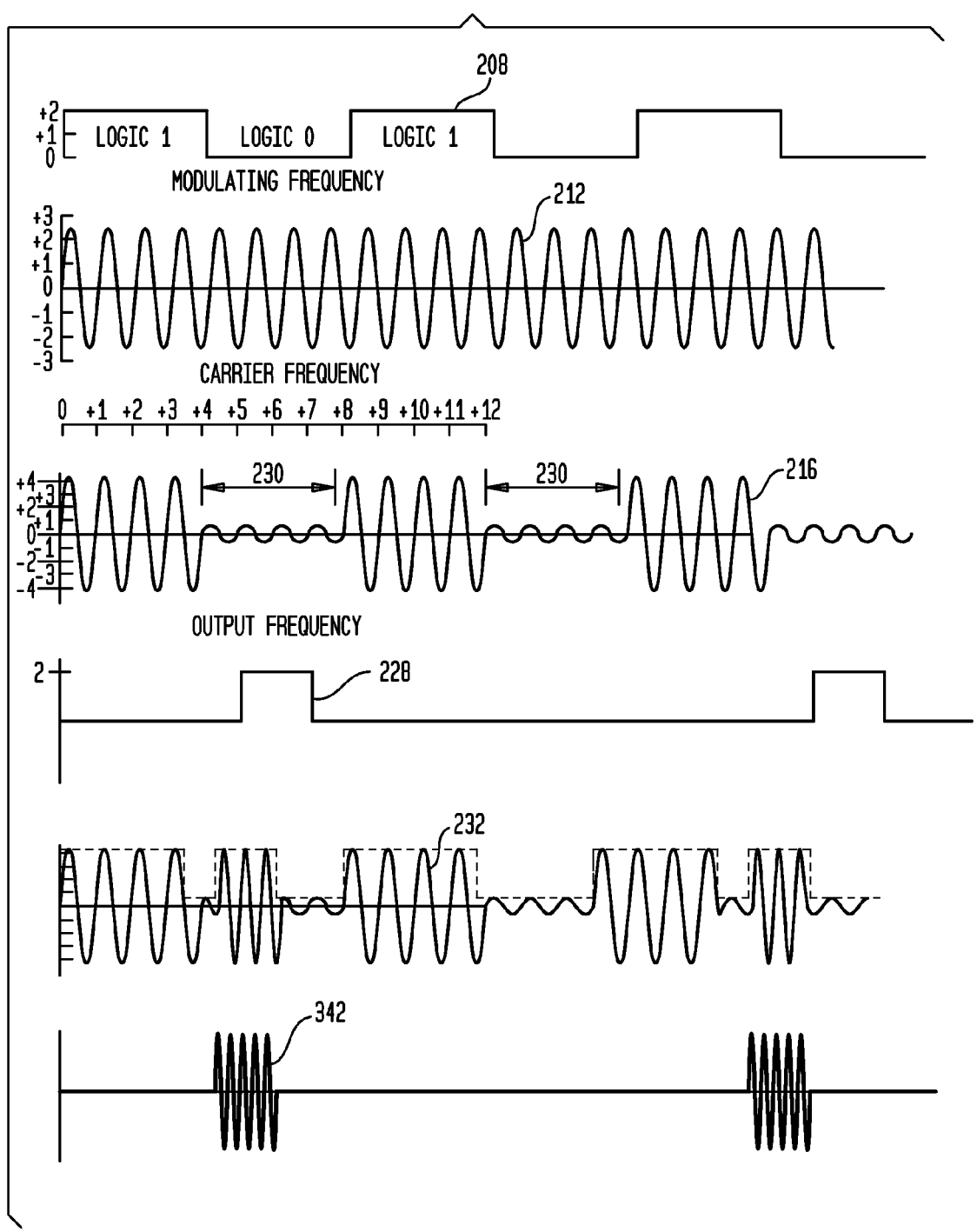
FIG. 5 shows exemplary waveforms generated by the implantable pulse generator shown in FIG. 4.

Referring to FIGS. 4 and 5, the first waveform generator 206 generates the first waveform 208 or signal having a frequency known to stimulate a first selected body part, such as a pudendal nerve, which is known to be stimulated by a frequency approximately within the range of 10-30 Hz. As indicated above, it has been proven difficult to pass such a low frequency signal through body tissue to reach certain target nerves with sufficient current density to stimulate the target nerves. To address this problem, the second waveform generator 210 generates a higher frequency carrier waveform 212, which is applied along with the first waveform 208 to an amplitude modulator 214, such as an On-Semi MC1496 modulator sold by Texas Instruments. The first waveform 208 is preferably a square wave having a frequency of approximately 10-30 Hz, and the second waveform 212 is preferably a sinusoidal signal having a frequency in the range of 10400 KHz. The modulation of the first waveform 208 with the second waveform (carrier waveform) 212 results in a modulated waveform or signal 216 having generally the configuration shown in FIG. 5. The signals shown in FIG. 5 are for illustrative purposes only, and are not intended as true representations of the exemplary signals described herein.

In operation, the modulated signal 216 generated by modulator 214 is transmitted through lead 218 to electrodes 220. In turn, the electrodes 220 apply the modulated signal 216 to the target nerve 222. As is readily understood by those skilled in the art, the use of the modulated signal 216 provides for efficient stimulation of the target nerve 222 due to the high frequency nature of the carrier waveform enabling the low frequency signal to be detected (and responded to) by the target nerve.

Referring to FIG. 5, it has been observed that the modulated signal 216 has periodic periods of inactivity 230. Rather than using the IPG (FIG. 4) to selectively stimulate only one target nerve, the periodic periods of inactivity 230 of the modulated signal 216 can be taken advantage of to generate a second modulated signal adapted to stimulate a second target nerve or other body part. Referring to FIGS. 4 and 5, to accomplish this, the third waveform generator 226 generates the third waveform 228 having a frequency that is different than the first waveform 208 and that is specifically selected to stimulate a second nerve or body part. An exemplary third waveform 228 is shown in FIG. 5. The third waveform 228 is desirably out of phase with the first waveform 208 to avoid interfering with the first modulated signal 216. Further, in one embodiment of the present invention, if the frequency ranges that simulate the first and second nerves overlap, the third waveform 228 can be generated or applied during the refractory period of the first nerve to ensure that the first nerve does not respond to the second modulated signal.

The first and third waveform generators 206, 226 preferably generate their respective waveforms 208, 228 out of phase with each other so that when combined with the carrier waveform 212, they appear along separate and discrete portions of the signal package 232 (FIG. 5), and each of the first and third waveforms have a frequency selected to specifically target different nerves or body portions. For example, the first waveform 208 may have a frequency of 20 Hz, which is known to have an effect on the autonomic element branches of the pudendal nerve (for affecting an overactive bladder), and the third waveform 228 may have a frequency of 10 Hz, which is known to have an effect on the somatomotor branch of the pudendal nerve (useful in treating intersticial cystitis). To the extent there is an overlap in frequency ranges, the third waveform 228 may be applied during the refractory period of the first nerve.

By the system and method described above, individual components of the modulated signal package can be used to selectively target different nerves, different nerve branches, different muscles, or selected other body parts. That is, a single IPG could provide stimulation signals designed to relieve multiple different symptoms such as those associated with pain management, overactive bladder, fecal incontinence, interstitial cystitis and any other pelvic floor disorder.

Figure 6:
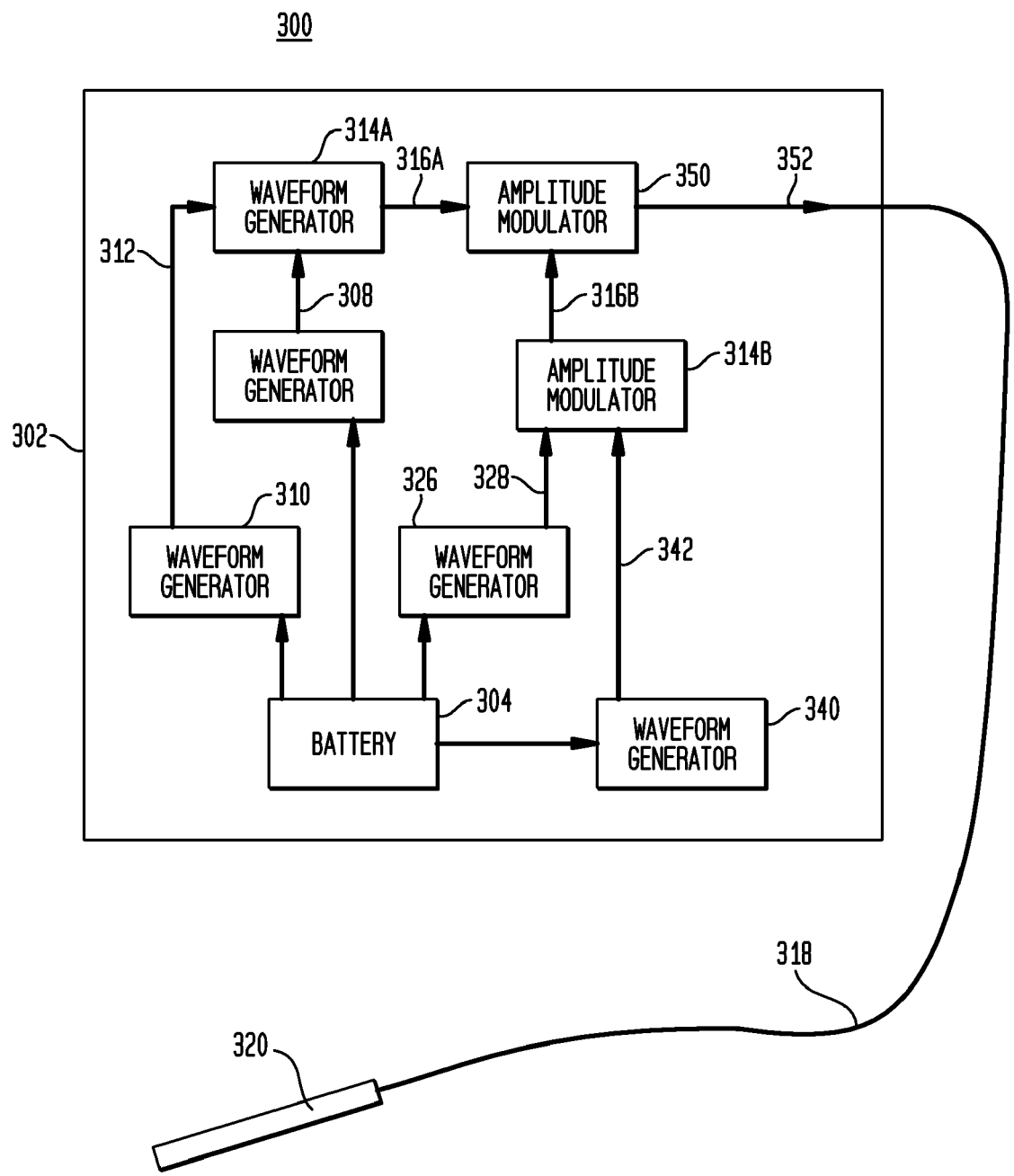
FIG. 6 shows an implantable pulse generator for stimulating body parts, in accordance with yet another preferred embodiment of the present invention.
Figure 7:
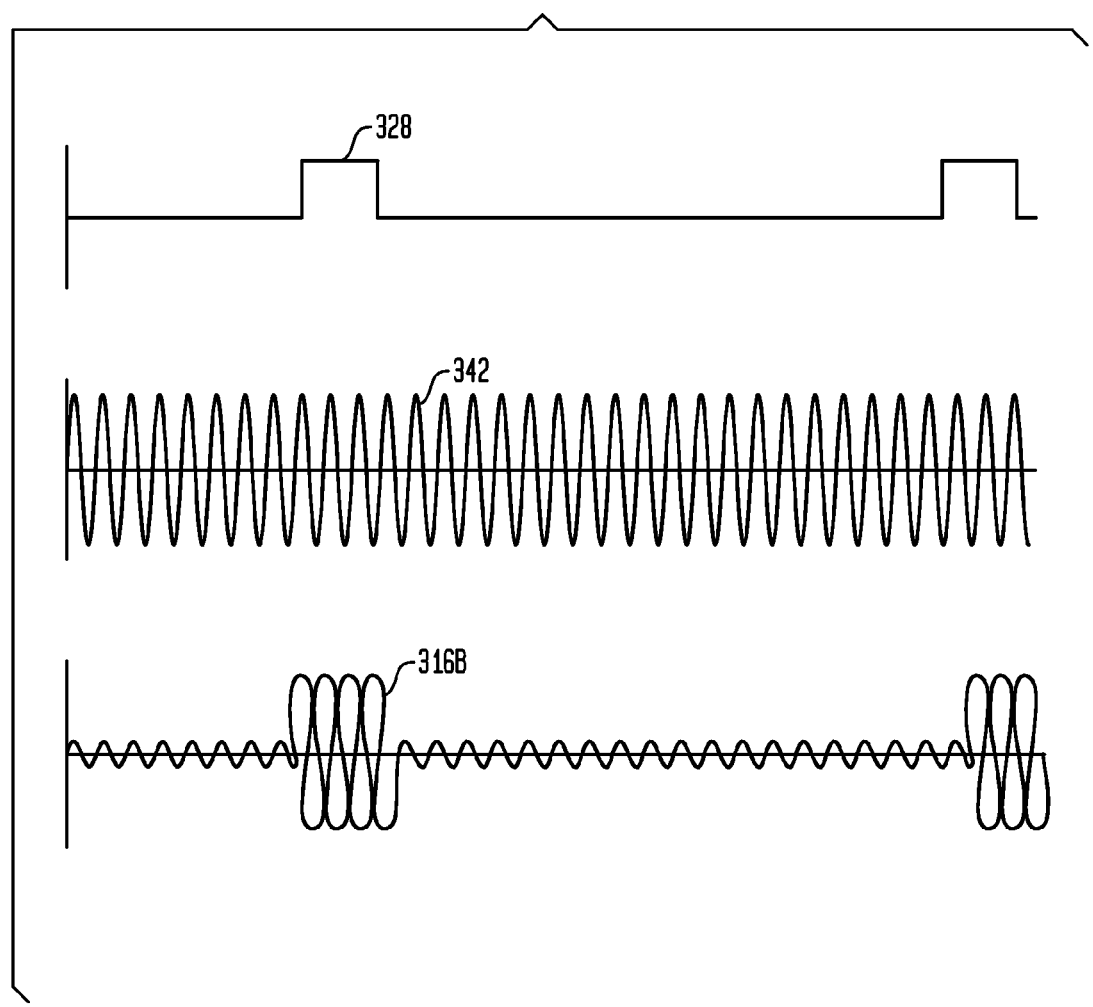
FIG. 7 shows exemplary waveforms generated by the implantable pulse generator shown in FIG. 6.

Those skilled in the art will recognize that the appropriate signals may be manipulated in many different ways to achieve suitable modulated signals and/or signal packages. For example, referring to FIGS. 5 and 6, in one embodiment of the present invention, a fourth waveform generator 340 may also be included that generates a fourth carrier waveform 342 having a frequency different from the second carrier waveform. This may be desirable if stimulation of the first and second nerve or body part will require the signal(s) to pass through different types or amounts of tissue. As illustrated, in embodiments using a single amplitude modulator, the fourth carrier waveform 342 is preferably applied only during periods of inactivity of the first waveform 308 to avoid affecting modulated signal 316A. In the embodiment of FIG. 6, the first waveform 308 and the second carrier wave 312 may be provided to a first amplitude modulator 314A to generate a first modulated waveform 316A. Referring to FIGS. 6 and 7, the third waveform 328 and the fourth carrier waveform 342 may be provided to a second amplitude modulator 314B to generate a second modulated waveform 316B. These first and second modulated waveforms may be further modulated by a third amplitude modulator 350 to create a signal package 352 that can be transmitted through lead 318 to electrodes 320. In one embodiment of the present invention, the first and second modulated signals 316A, 316B may be applied through separate first and second electrodes (not shown). In one or more other embodiments of the present invention, when the modulated waveforms have periods of inactivity, additional signals may be inserted into these non-active periods to target other nerves, muscles, or body parts.

Figure 8:
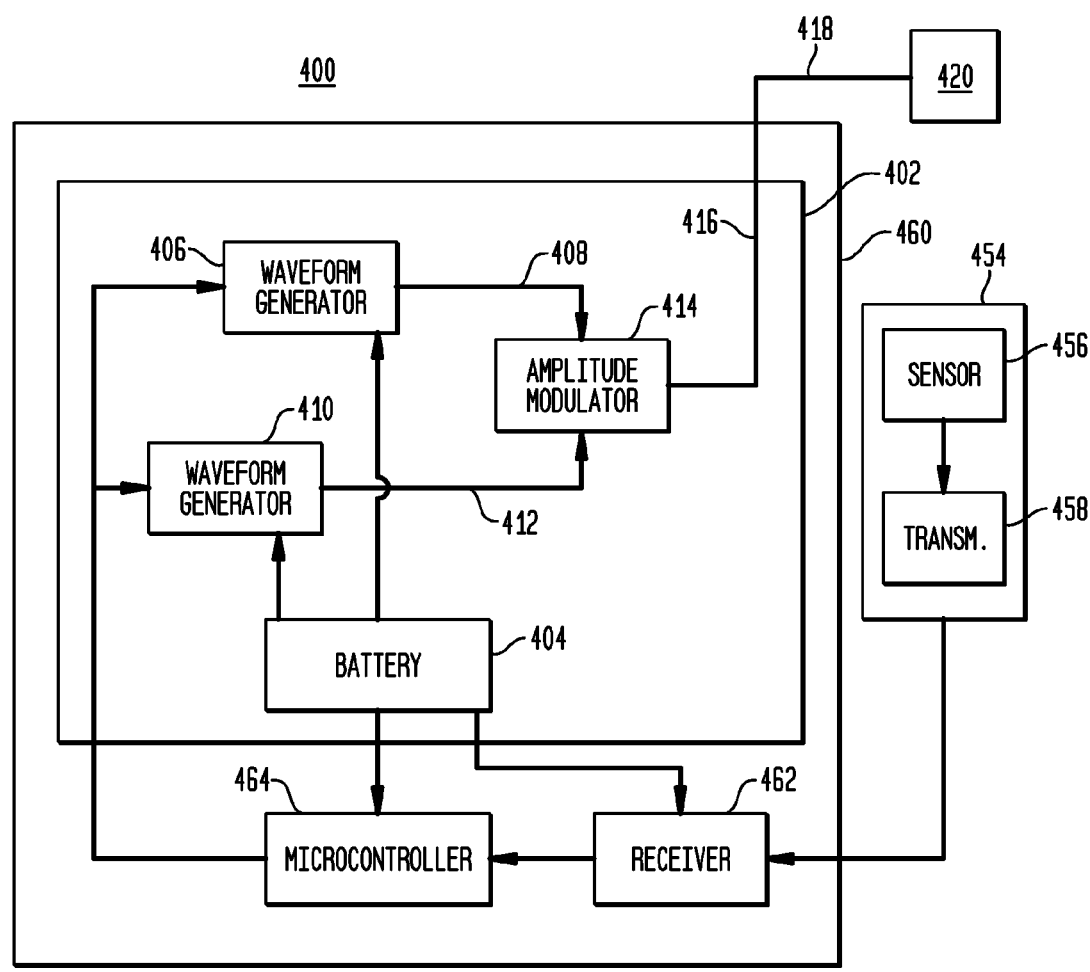
FIG. 8 shows an implantable pulse generator for stimulating body parts, in accordance with still another preferred embodiment of the present invention.

Referring to FIG. 8, in one embodiment of the present invention, the implantable pulse generator 400 has one or more biofeedback mechanisms. The biofeedback mechanisms desirably provide feedback to the system, and enable selective, as opposed to constant, operation of the system. As a result, nerve stimulation may only occur when necessary.

The IPG 400 includes a housing 402, a power source 404, such as a battery, a first waveform generator 406 that generates a first waveform 408, and a second waveform generator 410 that generates a second waveform 412. The first and second waveform generators 406, 410 are electrically coupled to and powered by the battery 404. The waveform generators 406, 410 may be of any suitable type, such as those sold by Texas Instruments of Dallas, Tex. under model number NE555. The first waveform generator 406 generates a first waveform 408 having a frequency known to stimulate nerves in the body. In one embodiment, the frequency is within the range of about 10-30 Hz. In another embodiment, the frequency is within the range of about 10-40 Hz. As noted above, such low frequency signals (e.g. 1040 Hz.) cannot, in and of themselves, pass through body tissue to effectively stimulate target nerves. In order to overcome this problem, the implantable pulse generator 400 has a second waveform generator 410 that generates a second waveform 412 having a higher frequency (e.g. 10-400 KHz.) that is applied along with the first waveform 408 to an amplitude modulator 414, such as the modulator having the designation On-Semi MC1496, which is sold by Texas Instruments.

The modulator 414 generates a modulated waveform 416 that is transmitted through a lead 418 to electrodes 420. In certain preferred embodiments, the lead 418 is flexible. The electrodes 420, in turn, apply the modulated waveform 416 to the target nerve (not shown) to stimulate the target nerve.

The IPG 400 also includes one or more sensor devices 454 that are preferably implantable within the body. The sensor devices 454 preferably include at least one sensor 456 that will sense a selected bio-physiological property, and a data transmission device 458 that transmits data or information gathered by the sensor 456 back outside the body to be further processed as described more fully below.

Figure 9:
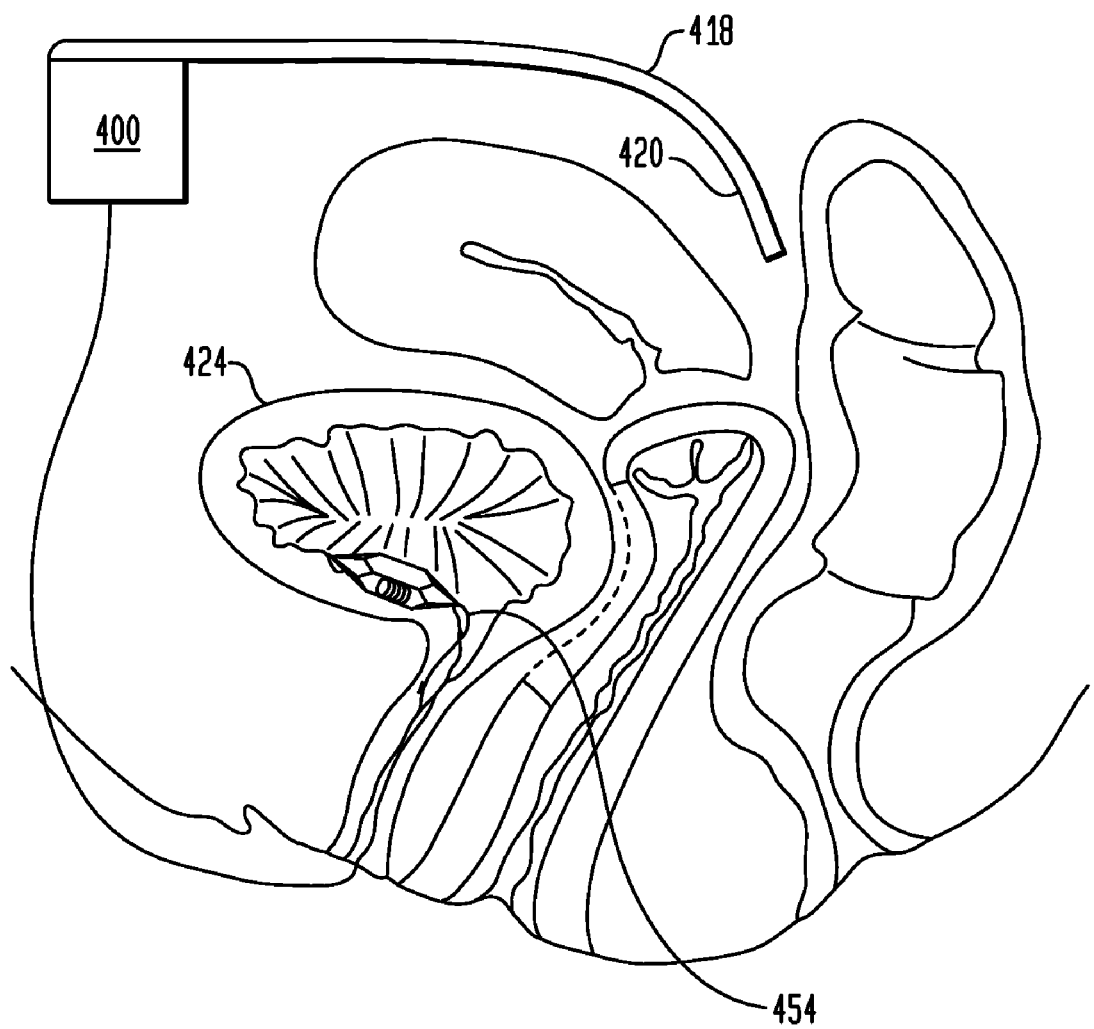
FIG. 9 shows the implantable pulse generator of FIG. 8 after being implanted in a body.

In one embodiment, the signal transmitter 458 is part of a larger signal control system 460 that further includes a receiving device 462 such as a MAX1472 from Maxim Semiconductors of Sunnyvale, Calif., that is electrically coupled to and powered by the battery 404. The receiving device 462 receives data from the one or more sensor devices 454 and provides this data to a microcontroller 464. The microcontroller is preferably programmed to receive and analyze the data, and based on this data to provide input to the first and second waveform generators 406, 410 to thereby control signal transmission by the IPG 400. Referring to FIGS. 8 and 9, the biofeedback sensor 454 may be a pressure sensor that is implanted within the body such as within the bladder 424. As is well known to those skilled in the art, measuring the pressure within the bladder over time may indicate the existence and magnitude of bladder contractions. When such pressure measurements indicate spastic bladder muscle activity (as compared to normal bladder contractions which will result in a slow and steady rise of pressure within the bladder), a feedback signal can be transmitted to the receiving device 462 and subsequently to the microcontroller 464. In response to the received feedback signals, the microcontroller 464 will, via control of the waveform generators 406, 410, cause the electrode(s) 420 to transmit the modulated signal. Receipt of the modulated signal by the target nerve (e.g. the pudendal nerve) will innervate the bladder muscles to substantially eliminate the spastic muscle contractions.

In one embodiment, the biofeedback device 454 may include multiple electronic components including a power source, one or more sensor components, and an electronic interface, each of which are electrically coupled to one another and mechanically mounted on a printed circuit board in a manner well known in the art. The one or more sensor components sense predetermined physiological properties within the body, and transmit signals or data representing such properties to the electrical interface. The system may include a data storage element for storing data correlating to the sensed physiological properties, but may also include a transmitter for transmitting the data external of the patient's body so that it can be used to control generation of the modulated signal as described above. The biofeedback device may be substantially surrounded by a collapsible housing or cage.

In one preferred embodiment of the present invention, the biofeedback device preferably remains within the body (e.g. the bladder) for an extended period of time to provide constant feedback that is used to control operation of the electrode. Where constant feedback is not used, the implantable sensors described herein may nevertheless be used to obtain data useful in rendering an accurate diagnosis and/or appropriate treatment. In one embodiment of the present invention, the device may remain within the bladder for 1-2 days, with pressure measurements being taken every ½ second. The type and frequency of pressure changes can be subsequently analyzed to provide feedback to assess body function. For example, vesicle pressure measured over time can reveal voiding times and frequency, can provide an indication of an overactive bladder, or of bladder overfilling. In one embodiment, the sensor element(s) are designed to operate in an extended sleep mode, "waking up" at fixed intervals of time to measure pressure or the like. Once sufficient data has been gathered, the device can subsequently be removed from the bladder such as by inserting a catheter into the bladder to retrieve the implantable device, or using the operating channel of a cystoscope or other suitable instrument to retrieve the device. The catheter or cystoscope would be inserted into the bladder, and the device grasped and pulled back into the catheter or cystoscope channel and subsequently removed from the body.

In one preferred embodiment of the present invention, the biofeedback system (exclusive of the housing) has an overall size of about 0.65-10 mm in diameter D, and about 0.65-10 mm in length L. In a preferred embodiment, the sensor component is a micro-miniature piezo-resistive pressure transducer for measuring pressure within a patient's body (e.g. within the bladder). A suitable transducer is an MPX series pressure sensor from Motorola of Schaumburg, Ill. Other suitable components may include the MSP430F149 microcontroller from Texas Instruments, Inc. of Dallas, Tex. that can be used to acquire, filter and store data from the pressure sensor, and power source such as any suitable biocompatible lithium battery. Although particular suitable electronic components have been named above, many others also exist and could be incorporated into the present invention. As indicated, the electronic components are preferably mounted on printed circuit board. Subsequently, the components and circuit board can be covered or encapsulated in silicone or other suitable covering to protect them from the environment, such as the fluid environment in the bladder Under these circumstances, the biofeedback device may further incorporate a data storage device in addition to or in place of the transmitter for storing rather than transmitting the data. The data can be subsequently retrieved and manipulated, preferably by uploading the data to a PC based software application in any suitable manner, such as wirelessly, for example, via an infrared data acquisition unit such as ENDEC HSDL-7001 and an IrDA transceiver HSDL-3202 interfaced to the microprocessor, via radio frequency acquisition, or via a hard wire connection such as through an RS232 interface.

Referring to FIG. 8, in embodiments utilizing biofeedback data, the receiver 462 may receive feedback data from more than one biofeedback device 454. In these embodiments, a second implantable biofeedback sensor similar to that shown and described above may be inserted into another body orifice (e.g. vaginal canal). The second biofeedback sensor may be encapsulated in a "tampon-like" device or casing that is made of rolled up or bound cotton, similar to a tampon. In one embodiment, the second implantable biofeedback device senses abdominal pressure, and the first implantable biofeedback device senses bladder pressure. As a result, the detrusor pressure (i.e. the pressure of the muscle lining of the wall of the bladder tissue) can be determined by subtracting the bladder pressure from the abdominal pressure. As is well known to those skilled in the art, a rise in detrusor pressure occurs when a patient strains, coughs, sneezes, laughs, etc., and detection of these pressures are clinically significant in the diagnosis of various bladder and lower urinary tract disease states. For example, the frequency of detrusor pressure increases provides meaningful data for assessing urge incontinence.

In one embodiment of the present invention, an IPG has a first implantable biofeedback sensor and a second implantable biofeedback sensor. One of the implantable biofeedback sensors transmits data to the implantable biofeedback sensor, which then wirelessly transmits both sets of data to a receiver 462 (FIG. 8).

Figure 10:
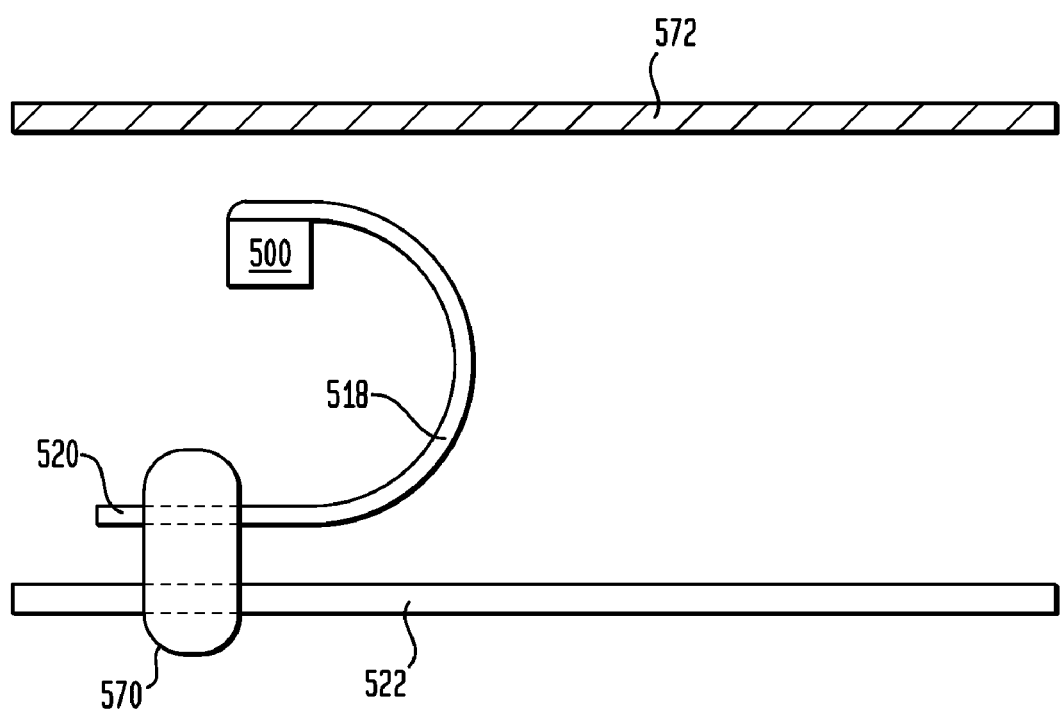
FIG. 10 shows an implantable pulse generator for stimulating body parts, in accordance with yet further preferred embodiments of the present invention.

Referring to FIG. 10, in one embodiment of the present invention, conductance of the stimulation energy from the electrode(s) to the target nerve or body part can be increased by the placement of a conductive tract 570 that may extend either fully or partially from the electrode(s) to the target nerve or body part. The conductive tract may be a cross-linked polyacrylaride gel such as the Aquamid® injectable gel from Contura of Denmark. This bio-inert gel, injected or otherwise inserted, is highly conductive and may or may not be an aqueous solution. The implanted gel provides numerous benefits including ease of delivery, less invasiveness and patient comfort as the gel is not rigid and can conform to the patient's body. As stated above, the clear advantage of the injected gel tract is a highly conductive path from the electrode(s) to the target nerve that is much more conductive than the surrounding tissue. This reduces energy dispersion and increases the efficiency of the energy transfer between the electrode(s) and the target nerve.

As shown in FIG. 10, the implantable pulse generator (IPG) 500 is implanted under the skin 572 of a mammal, such as a human. The IPG 500 includes a lead 518 having one or more electrodes 520 at a distal end thereof. The electrodes 520 are preferably positioned in the vicinity of a target nerve 522. The conductive gel 570 extends between the electrodes 520 and the target nerve 522. One advantage of using a conductive gel is that wire or needle electrodes can only come in proximity to one plane of the target nerve, whereas the deformable and flowable conductive gel 570 can envelope the target nerve 522. As a result, the conductive gel 570 can be in electrical and physical contact with the full 360 degrees of the target nerve, thereby enhancing application of the modulated waveform to the target nerve. In one embodiment, the conductive gel may extend from a location substantially in contact with the target nerve to a location closer to the outer skin layer 572. In one or more embodiments, multiple conductive gel pockets or tracts in any configuration may be used.

Although one suitable conductive gel has been described above, various others are also suitable. Many thermoset hydrogels and thermoplastic hydrogels could be used as well. Examples of thermoset hydrogels include cross-linked varieties of polyHEMA and copolymers, N-substituted acrylamides, polyvinylpyrrolidone (PVP), poly(glyceryl methacrylate), poly(ethylene oxide), poly(vinyl alcohol), poly(acrylic acid), poly(methacrylic acid), poly(N, N-dimethylaminopropyl-N'-acrylamide), and combinations thereof with hydrophilic and hydrophobic comonomers, cross-linkers and other modifiers. Examples of thermoplastic hydrogels include acrylic derivatives such as HYPAN, vinyl alcohol derivatives, hydrophilic polyurethanes (HPU) and Styrene/PVP block copolymers.

While the foregoing is directed to embodiments of the present invention, other and further embodiments of the invention may be devised without departing from the basic scope thereof.

What is claimed is:

1. An implantable pulse generator for stimulating nerves comprising:
   a first waveform generator adapted to generate a first waveform having a first frequency;
   a second waveform generator adapted to generate a carrier waveform having a second frequency that is higher than said first frequency;
   a modulator electrically coupled to said first and second waveform generators and adapted to modulate said first waveform and said carrier waveform to generate a modulated waveform;
   a surgically implantable housing containing said first and second waveform generators and said modulator;
   a lead electrically coupled with said modulator and extending from said surgically implantable housing; and
   an electrode connected to a distal end of said lead and electrically coupled to said modulator for applying said modulated waveform transmitted through said lead.

2. The implantable pulse generator as claimed in claim 1, wherein said lead is a flexible lead, and wherein said first waveform has a frequency adapted to stimulate a target nerve.

3. The implantable pulse generator as claimed in claim 1, wherein said first waveform has a frequency substantially within the range of 10-40 Hz.

4. The implantable pulse generator as claimed in claim 1, wherein said carrier waveform has a frequency substantially within the range of 10-400 KHz.

5. The implantable pulse generator as claimed in claim 1, further comprising a microprocessor adapted to receive biofeedback data and control operation of said first and second waveform generators in response to said biofeedback data.

6. The implantable pulse generator as claimed in claim 5, further comprising a receiving device adapted to receive said biofeedback data, said receiving device being in communication with said microprocessor for providing said biofeedback data thereto.

7. The implantable pulse generator as claimed in claim 6, further comprising at least one sensor in communication with said receiving device, said at least one sensor being adapted to sense one or more physiological conditions of a mammal.

8. The implantable pulse generator as claimed in claim 7, further comprising a transmitter coupled with said at least one sensor for transmitting said one or more sensed physiological conditions.

9. The implantable pulse generator as claimed in claim 1, further comprising:
a third waveform generator adapted to generate a third waveform having a third frequency that is different from and out of phase with said first waveform;
said modulator being electrically coupled with said third waveform generator and being adapted to modulate said carrier, first and third waveforms to generate said modulated waveform.

10. The implantable pulse generator as claimed in claim 9, wherein said first waveform is adapted to stimulate a first target nerve and said third waveform is adapted to stimulate a second target nerve.

11. The implantable pulse generator as claimed in claim 9, wherein said first waveform is adapted to stimulate a first body part and said third waveform is adapted to stimulate a second body part.

12. The implantable pulse generator as claimed in claim 11 further comprising a power source disposed within said surgically implantable housing for providing power to said waveform generators and said modulator.

13. The implantable pulse generator as claimed in claim 9, wherein said first waveform has a frequency of approximately 20 Hz, said third waveform has a frequency of approximately 10 Hz, and said carrier waveform has a frequency of approximately 10-400 KHz.

14. The implantable pulse generator as claimed in claim 9, further comprising a fourth waveform generator adapted to generate a fourth carrier waveform having a frequency different than said second carrier waveform, and wherein said modulator further modulates said fourth carrier waveform to generate a modulated signal package.

15. The implantable pulse generator as claimed in claim 14, wherein said modulator further comprises:
a first modulator for modulating said first waveform and said second carrier waveform to generate a first modulated signal;
a second modulator for modulating said third waveform and said fourth carrier waveform to generate a second modulated signal; and
a third modulator for modulating said first and second modulated signals to generate a modulated signal package.

16. An implantable system for stimulating nerves comprising:
a first waveform generator adapted to generate a first waveform having a frequency capable of stimulating a body part;
a second waveform generator adapted to generate a carrier waveform having a second frequency capable of passing through tissue of a mammal;
a modulator electrically coupled to said first and second waveform generators and adapted to modulate said first waveform and said carrier waveform to generate a modulated waveform;
a power source for operating said system;
a surgically implantable housing containing said first and second waveform generators, said modulator, and said power source;
a lead electrically coupled with said modulator and extending from said surgically implantable housing; and
an electrode connected to a distal end of said lead and electrically coupled to said modulator for applying said modulated waveform transmitted through said lead.

17. The implantable system as claimed in claim 16, wherein said lead is a flexible lead, and wherein said first waveform has a frequency substantially within the range of 10-40 Hz, and said carrier waveform has a frequency substantially within the range of 10-400 KHz.

18. The implantable system as claimed in claim 16, further comprising:
a microprocessor adapted to receive biofeedback data and control operation of said first and second waveform generators in response to said biofeedback data; and
at least one sensor in communication with said microprocessor and being adapted to sense one or more physiological conditions of a mammal.

19. The implantable system as claimed in claim 16, further comprising:
a third waveform generator adapted to generate a third waveform having a third frequency that is different from and out of phase with said first waveform;
said modulator being electrically coupled with said third waveform generator and being adapted to modulate said carrier, first and third waveforms to generate said modulated waveform.

20. The implantable system as claimed in claim 19, wherein said first waveform is adapted to stimulate said first body part and said third waveform is adapted to stimulate a second body part.

21. A method for stimulating body parts comprising:
providing an implantable pulse generator including
a first waveform generator adapted to generate a first waveform having a first frequency capable of stimulating a body part,
a second waveform generator adapted to generate a carrier waveform having a frequency capable of passing through tissue of a mammal,
a modulator electrically coupled to said first and second waveform generators and adapted to modulate said first waveform and said carrier waveform to generate a modulated waveform,
a power source for providing power to said first and second waveform generators and said modulator,
a housing containing said first and second waveform generators, said modulator and said power source,
a flexible lead electrically coupled with said modulator and extending from said housing, and
an electrode connected to a distal end of said flexible lead and electrically coupled to said modulator for applying said modulated waveform;
surgically implanting said housing in a mammal;
generating said first waveform and said carrier waveform;
modulating said first waveform with said carrier waveform to produce a modulated signal;

transmitting said modulated signal through said flexible lead to said electrode;

applying said modulated signal through said electrode to said body part.

22. The method as claimed in claim 21, wherein said first waveform has a frequency substantially within the range of 10-40 KHz, and said carrier waveform has a frequency substantially within the range of 1-0-400 KHz.

23. The method as claimed in claim 21, further comprising:
implanting a sensor in said mammal;
obtaining biofeedback data using said sensor; and
using said biofeedback data for controlling generation of said first and second waveforms by said first and second waveform generators.

24. The method as claimed in claim 21, wherein said implantable pulse generator includes a third waveform generator adapted to generate a third waveform having a frequency capable of stimulating a second target nerve, the method further comprising:

generating said third waveform out of phase with said first waveform;

modulating said first waveform, said carrier waveform, and said third waveform to create a modulated signal package; and applying said modulated signal package to one or more body parts of said mammal.

25. The method as claimed in claim 24, further comprising generating a fourth carrier waveform having a frequency different than said second carrier waveform, wherein the modulating step comprises modulating said first waveform and said second carrier waveform to create a first modulated signal, and modulating said third waveform and said fourth carrier waveform to create a second modulated signal.

26. The method as claimed in claim 21, further comprising applying a conductive tract subcutaneously between said electrode and said body part.

* * * * *